(12) United States Patent
Sekine et al.

(10) Patent No.: US 6,527,753 B2
(45) Date of Patent: Mar. 4, 2003

(54) ENDOSCOPIC TREATMENT SYSTEM

(75) Inventors: Ryuta Sekine, Chofu (JP); Christopher J. Gostout, Northeast Rochester, MN (US)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/794,974

(22) Filed: Feb. 27, 2001

(65) Prior Publication Data

US 2001/0049509 A1 Dec. 6, 2001

Related U.S. Application Data

(60) Provisional application No. 60/185,729, filed on Feb. 29, 2000.

(51) Int. Cl.[7] .......................... A61M 5/00; A61M 25/00
(52) U.S. Cl. ........................ 604/264; 604/614; 604/615; 600/104; 600/106; 600/107
(58) Field of Search ................................ 604/615, 264, 604/614; 600/104, 106, 107

(56) References Cited

U.S. PATENT DOCUMENTS

| | | | |
|---|---|---|---|
| 5,846,182 A | * | 12/1998 | Wolcott ...................... 600/114 |
| 5,855,549 A | * | 1/1999 | Newman ..................... 604/515 |
| 6,022,313 A | * | 2/2000 | Ginn et al. .................. 600/104 |

FOREIGN PATENT DOCUMENTS

| | | |
|---|---|---|
| JP | 6-75402 | 10/1994 |
| JP | 9262239 A | * 10/1997 |
| JP | 200033071 A | * 2/2000 |

* cited by examiner

*Primary Examiner*—Robin O. Evans
(74) *Attorney, Agent, or Firm*—Frishauf, Holtz, Goodman & Chick, P.C.

(57) ABSTRACT

This invention provides an endoscopic treatment system for executing at least one of localized injection through mucous membrane, peeling off and cutting off of mucous membrane. This system has an endoscope, which has an insertion section provided with at least one channel extending therein. The system also has a plurality of treatment tools including a syringe needle for executing localized injection through a portion of mucous membrane, forceps for gripping a portion of mucous membrane, and at least one knife for executing at least one of peeling off and cutting off of mucous membrane. Further, this system includes an endoscopic guide tube to be inserted into the esophagus, which has a main channel for inserting therein the endoscope, and at least one sub channel for inserting therein each of the treatment tools.

10 Claims, 5 Drawing Sheets

ENDOSCOPIC TREATMENT SYSTEM

CROSS-REFERENCE TO RELATED APPLICATIONS

This application claims the benefit of U.S. Provisional Application No. 60/185,729, filed Feb. 29, 2000.

BACKGROUND OF THE INVENTION

For the gastrointestinal tract including the esophagus and stomach, a treatment method for cutting off mucous membrane with an endoscope is widely adopted. Japanese Utility Model Application KOKAI Publication No. 6-75402 discloses a method for cutting off mucous membrane by sucking the mucous membrane into a transparent hood attached to the distal end of an endoscope, and constricting the base of the sucked membrane with a high frequency snare introduced into the endoscope.

For the esophagus, an attempt is being made to use a method for cutting off mucous membrane with a combination of a sheath 1 and an endoscope 2 as shown in FIG. 1. In general, the sheath 1 used for this method has a guide channel 3 for inserting therein the endoscope 2, a guide channel 4 for inserting therein a high frequency snare 5, and an obliquely cut distal end. A space between the endoscope 2 inserted in the guide channel 3 and the sheath 1 is sealed at the proximal end side (not shown). When using it, at first, the sheath 1 is inserted into the esophagus and then, the endoscope 2 is inserted into the sheath 1. Mucous membrane 6 is sucked by the endoscope 2 into the guide channel 3 of the sheath 1, thereby constricting and cutting off the base of the mucous membrane 6 with the high frequency snare 5. There is a case where diseased mucous membrane is cauterized, instead of being cut, using argon beam plasma, a laser or a high frequency probe.

The above-described conventional methods can cut off diseased mucous membrane with a diameter of, at maximum, about 2 cm, and accordingly, their applicability is limited by the size of a diseased area. Especially, in the case of "Barrett Esophagus" which is a disease rapidly increasing, a columnar epithelium tissue to be cut off extends over almost the entire inner surface of the lumen at a location separated by 3–5 cm or more from the esphagogastric junction. Therefore, in the conventional methods, it is difficult to cut off, at one time, the entire tissue to be cut off, and hence it is necessary to divide such a large diseased area into portions and cut it off one by one.

BRIEF SUMMARY OF THE INVENTION

It is the object of the invention to provide an improved endoscopic treatment system capable of efficiently cutting off even a large diseased area.

According to an aspect of the present invention, there is provided an endoscopic treatment system for executing, at a predetermined portion of an esophagus, at least one of localized injection into submucosa, peeling off mucous membrane, and cutting off of mucous membrane. This system comprises an endoscope having an insertion section provided with at least one channel therein, the endoscope being used for observing a target inner portion of a body; and a plurality of treatment tools for treating the target inner portion. The treatment tools include a syringe needle for executing localized injection into submucosa, forceps for gripping mucous membrane, and at least one knife for executing at least one of peeling off mucous membrane and cutting off of mucous membrane. The at least one knife comprises one of a needle-shaped knife and a flat knife. This system further comprises an endoscopic guide tube to be inserted into the esophagus, and having a main channel for inserting therein the endoscope, and at least one sub channel for inserting therein each of the treatment tools. Thus, each of the treatment tools can be made to approach the target inner portion via one of the endoscope and the endoscopic guide tube.

In the system of the invention, a plurality of strip areas are formed in the esophageal mucous membrane by forming a plurality of longitudinal incisions and one circumferential incision in the esophageal mucous membrane, and are sequentially peeled off the esophagus. Thus, a wide area of esophageal mucous membrane can be reliably and completely peeled off. Moreover, the cut-off mucous membrane can be collected easily, which enables an efficient and accurate histological diagnosis of the cut-off mucous membrane.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

[First Embodiment]
(Structure)

Figure 1:
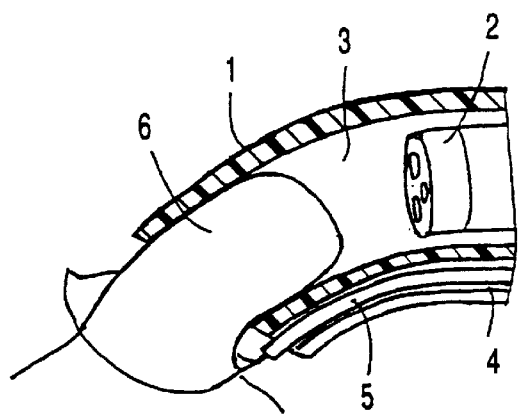
FIG. 1 is a schematic view illustrating a method for cutting off esophagus mucous membrane by a conventional technique.
Figure 2:
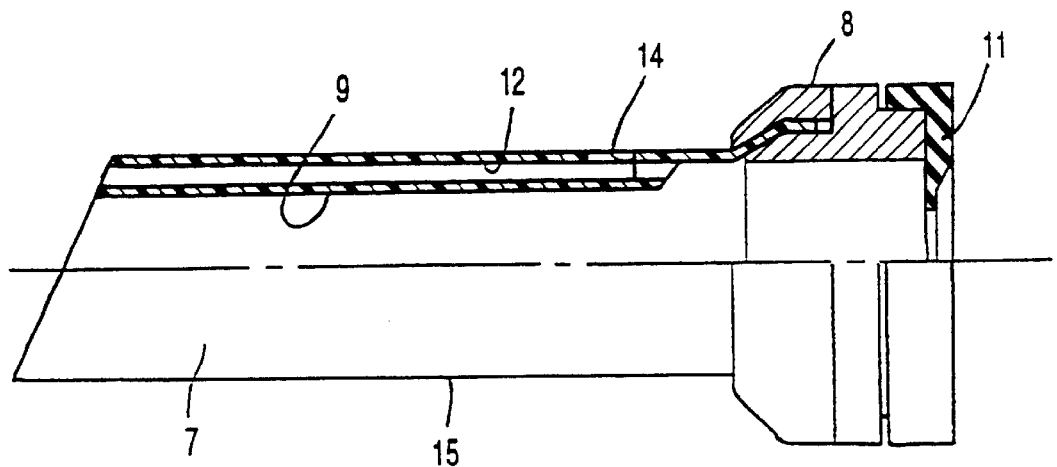
FIG. 2 is a fragmentary sectional view of an endoscopic guide tube according to a preferred embodiment of the invention.
Figure 3:
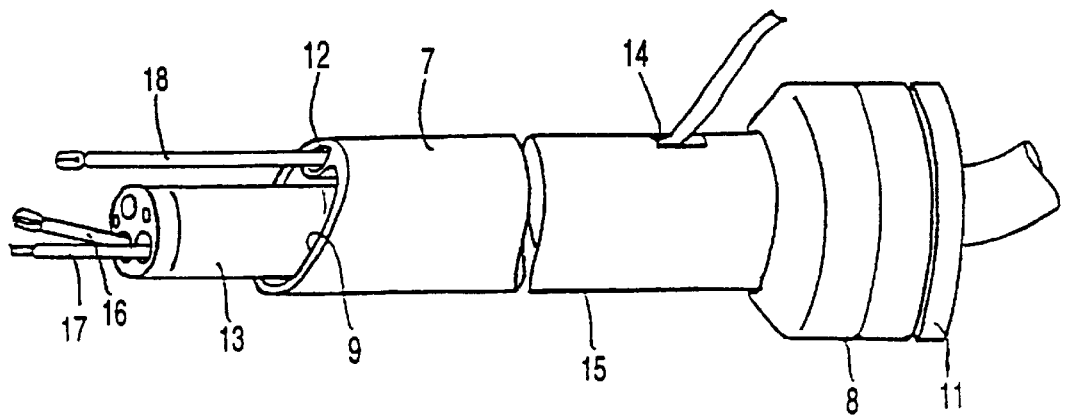
FIG. 3 is a schematic view illustrating the entire structure of a system according to a first embodiment, in which an endoscope and various treatment tools are inserted in the guide tube shown in FIG. 2.

FIGS. 2 and 3 show an endoscopic treatment system according to a first preferred embodiment of the invention. In the embodiments described below, like reference numeral denotes like element, and no duplicate description will be given thereof.

The system of the first embodiment is equipped with two-channel endoscope 13, which has two channels formed therein for inserting therein forceps for gripping mucous membrane or the needle of a syringe used to make an injection into a mucous membrane, and also for inserting therein a treatment tool such as a needle-shaped electric knife used to incise and cut off a portion of mucous membrane. The endoscope 13 is connected to an endoscope light source unit (not shown) and an endoscope photography apparatus (not shown). As is shown in the figures, the endoscope 13 is of a straight-sight type in which an observation window and an illumination window are located at its distal end, and the two channels open at the distal end. Although the endoscope of this type is preferable, the invention is not limited to it, but an endoscope of a so-called lateral-sight type or a squint type is also applicable.

Further, this system includes an endoscopic guide tube 15. The guide tube 14 has a soft and transparent insertion section 7 which can be inserted into the cavity of the esophagus through the mouth, is made of a resin and is substantially shorter than the effective length of the insertion section of the two-channel endoscope 13, and also has a grip section 8 provided at the proximal end of the insertion section 7. A main channel, i.e. an endoscopic guide channel 9, is formed through the endoscopic guide tube 15 from the grip section 8 to the distal end of the insertion section 7, so that the two-channel endoscope 13 can be inserted movably in both longitudinal and angular directions. A seal member 11 for preventing air from leaking through a gap between the endoscopic guide channel 9 and the inserted two-channel endoscope 13 is provided around the endoscopic guide channel 9 at the grip section 8. The endoscopic guide tube 15 also has a sub channel or forceps guide channel 12 extending along the endoscopic guide channel 9 from near the grip section 8 to the distal side of the insertion section, and to be used to insert therein forceps for gripping the mucous membrane; and a forceps port 14 opening to a side surface of the insertion section 7 and connecting the forceps guide channel 12 to the outside.

The system of the embodiment further includes forceps 16 to be inserted in one of the two channels of the endoscope 13; a needle-shaped electric knife 17 to be inserted in the other one of the two channels of the endoscope 13 and connected to a high frequency power supply (not shown); and forceps 18 to be inserted in the forceps guide channel 12 in the endoscopic guide tube 15 and used for gripping the mucous membrane.

(Operation)

FIGS. 4–8 are views useful in explaining how to treat the "Barrett Esophagus" using the endoscopic treatment system of the first embodiment. First, the two-channel endoscope 13 is inserted into the endoscopic guide tube 15 and then into the esophagus through the mouth and the throat, while looking through the endoscope. Subsequently, the endoscopic guide tube 15 is inserted into the esophagus along the two-channel endoscope 13. At this time, the "Barrett Esophagus" is confirmed through the two-channel endoscope 13, and the endoscopic guide tube 15 is forwarded until its distal end reaches a position near the diseased portion.

Figure 4:
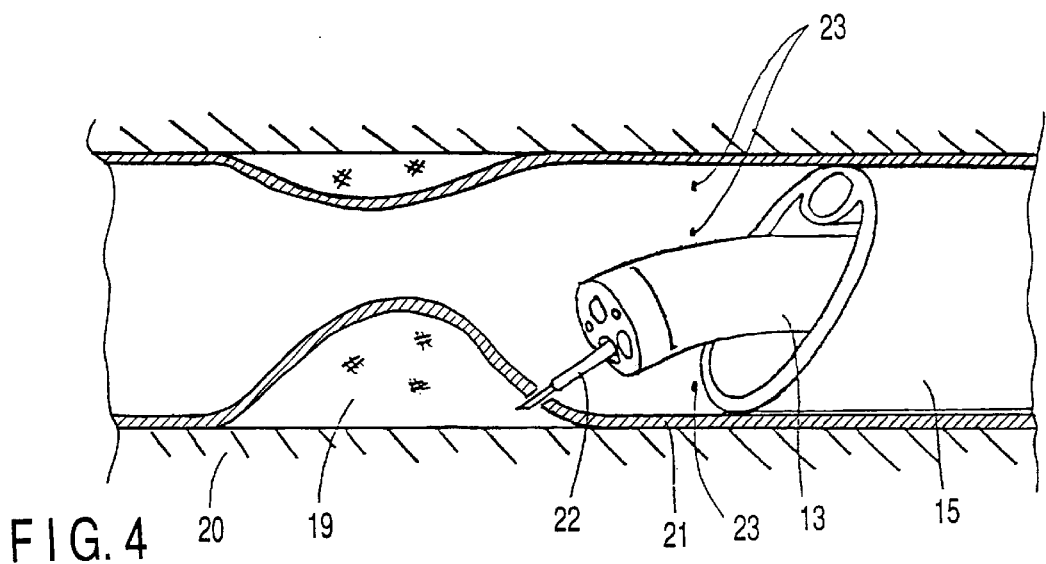
FIG. 4 is a view useful in explaining the step of raising a to-be-cut portion of the esophagus mucous membrane by localized injection using the system of FIG. 2.

FIG. 4 is a sectional view of the esophagus, showing the mucous membrane 21 and muscular tunics 20 of the esophagus. The needle-shaped electric knife 17 is inserted through one of the two channels of the endoscope 13, thereby cauterizing a to-be-incised "Barrett Esophagus" in a dotted manner to form markings 23. After that, the needle-shaped electric knife is removed from the endoscope 13, and is exchanged for a syringe needle 22. Using the syringe needle 22, a dextrose solution with a concentration of 50% is locally injected into esophageal submucosa 19 at the cardia side of the esophagus, to thereby separate the mucous membrane 21 from the muscular tunics 20 and raise it. This operation is repeated along the full circumference of the esophagus. Moreover, while the syringe needle 22 is shifted toward the throat end of the esophagus, and the operation is repeated, the esophageal mucous membrane of the entire inner surface of the esophagus is raised by localized injection up to the portion provided with the markings 23. Localized injection can be executed using, as well as the dextrose solution, a solution suitable for living tissue, such as a solution of another saccharide or physiological saline.

Figure 5:
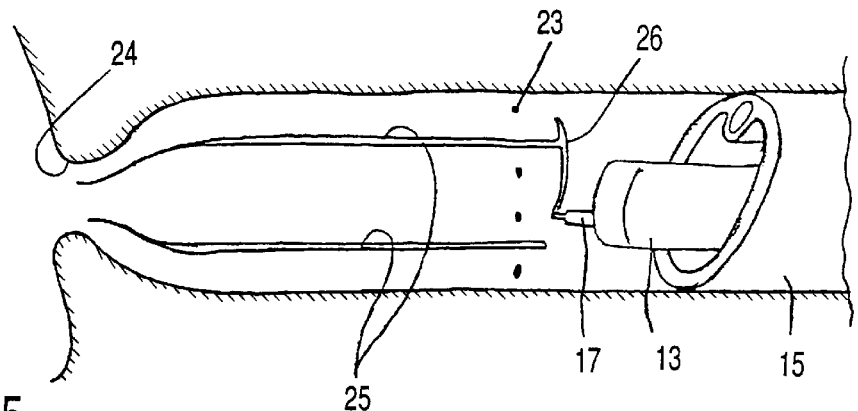
FIG. 5 is a view useful in explaining the step of forming longitudinal and circumferential incisions in a predetermined portion of the esophagus mucous membrane, using the system of FIG. 2.
Figure 6:
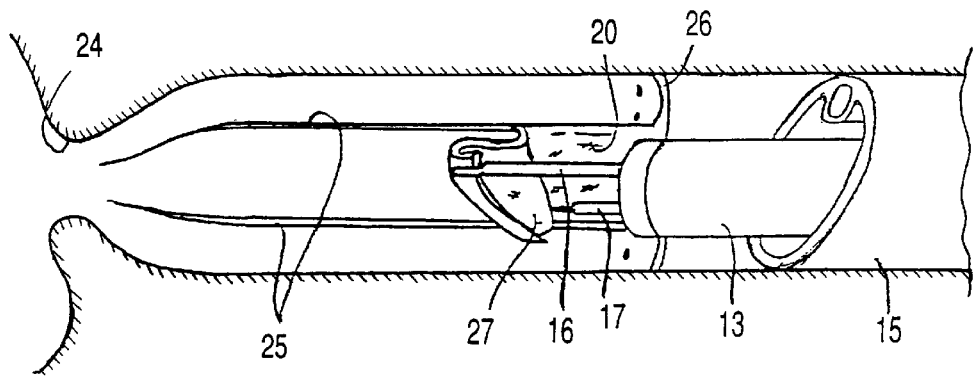
FIG. 6 is a view useful in explaining the step of peeling off a strip of mucous membrane along the incisions formed as shown in FIG. 5.
Figure 7:
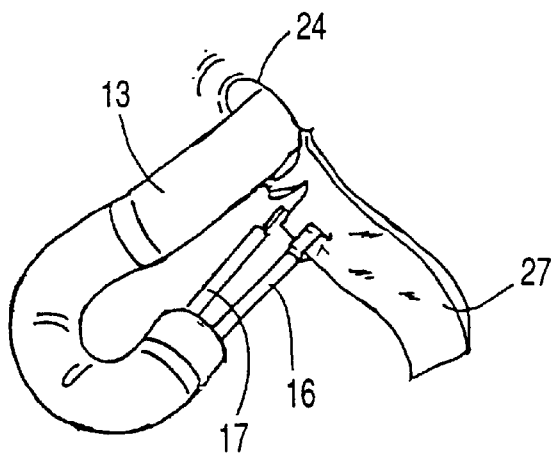
FIG. 7 is a view useful in explaining the step of cutting off a strip of mucous membrane hanging from the inner surface of the stomach.

FIGS. 5–7 show the manner of cutting off a portion of esophageal mucous membrane. Also in this case, the distal end of the two-channel endoscope 13 is inserted into a portion of the esophagus close to the cardia 24, thereby linearly incising the portion of the mucous membrane, which extends toward the throat end where the markings 23 are formed, along the longitudinal direction of the esophagus, using the needle-shaped electric knife 17. This incising operation is repeated several times to incise the mucous membrane into strips. The throat end of the esophageal mucous membrane incised into strips along the incisions 25 is incised along the full circumference. Reference numeral 26 denotes a circumferential incision, and reference numeral 27 the strip area of the mucous membrane incised along the incisions 25 and 26.

After that, the forceps 16 are inserted through the other channel of the endoscope 13, thereby gripping the free end of the strip area 27 adjacent to the circumferential incision 26. With the strip area 27 gripped with the forceps 16, the two-channel endoscope 13 is pushed into the stomach together with the forceps 16. As a result, the strip area 27 is completely separated from the muscular tunics 20. If it is hard to smoothly separate the area 27 from the muscular tunics 20, they are separated with the needle-shaped electric knife 17.

After the distal end of the two-channel endoscope 13 is introduced into the stomach, with the strip area 27 gripped, it is bent to observe the cardia 24 from the stomach side as shown in FIG. 7. The strip area 27 hangs into the stomach from the cardia 24. The portion of the strip area 27, which is close to the cardia 24, is now gripped with the forceps 16. Then, the area 27 is cut off by the needle-shaped electric knife 17 projecting from the other channel of the endoscope 13. Thereafter, the bent state of the distal end of the endoscope 13 is released to straighten the insertion section, while gripping the strip area 27 with the forceps 16.

The two-channel endoscope 13 is then removed from the endoscopic guide tube 15, together with the forceps 16 and the strip area 27 gripped with the forceps 16, thereby collecting the strip area 27. By repeating this operation, portions of the esophagus mucous membrane can be cut off along the full circumference over a wide area.

Figure 8:
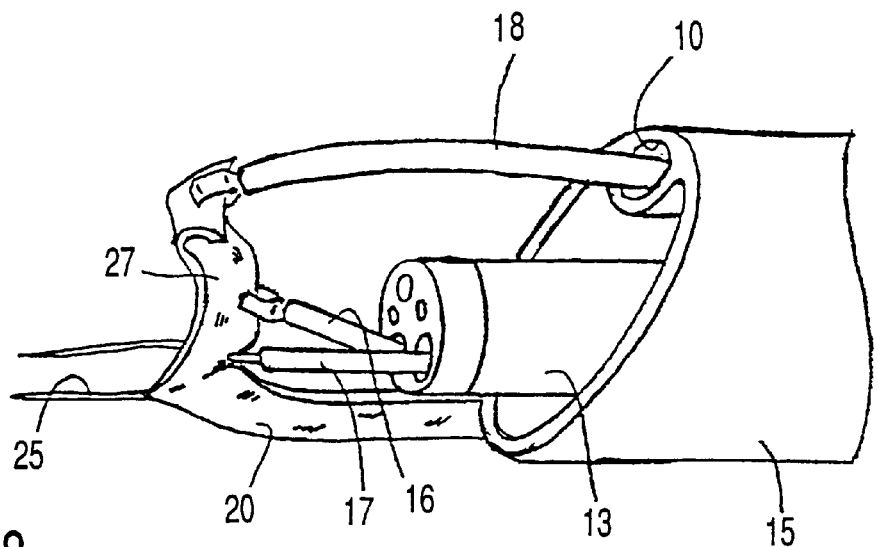
FIG. 8 is a view useful in explaining the step of separating a strip of mucous membrane from a muscular tunics, using a surgeon's knife.

When it is hard to peel the strip area 27 off the muscular tunics 20, the needle-shaped electric knife 17 is used to separate them, as is shown in FIG. 8. Further, where the strip area 27 is not completely peeled off, an already separated portion of the area 27 may interrupt the peeling operation. This being so, the strip area 27 is gripped and raised with the forceps inserted in the forceps guide channel 10, whereby it is moved toward the endoscopic guide tube 15. In this state, while looking through the twochannel endoscope 13, it is forwarded under the strip area 27 to approach a target portion and separate the area 27 from the muscular tunics 20.

Figure 9:
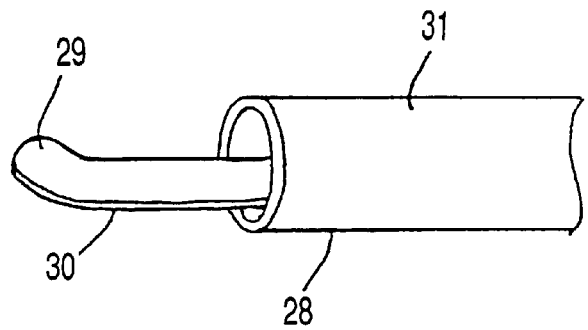
FIG. 9 is a view showing a modification of the surgeon's knife applicable to the system of FIG. 2.

A high frequency electric knife 28 as shown in FIG. 9 may be used instead of the needle-shaped electric knife 17. The high frequency electric knife 28 has a high frequency cutting section 29, which is in the shape of a plate and has its distal end slightly curved. The high frequency cutting section 29 is arranged to protrude from and retreat into a sheath 31 in accordance with the movement of an operating section (not shown), which is connected to a high frequency power supply. The reverse surface of the high frequency cutting section 29 is coated with an insulating layer 30 made of a resin material that is represented by a fluorocarbon resin such as polytetrafluoroethylene. When peeling off a portion of the esophagus mucous membrane using the high frequency electric knife 28 of this embodiment, efficient cutting off can be executed if the insulating layer 30 is kept in contact with the muscular tunics 20.

(Advantage)

Different from the conventional system, the system of the embodiment can cut off a target area of mucous membrane at one time in a reliable manner. Moreover, the operation of peeling of f a portion of mucous membrane can be executed more easily and in a shorter time than the conventional method. In addition, the endoscopic guide tube enables a smooth operation of the endoscope.

[Second Embodiment]

Figure 10:
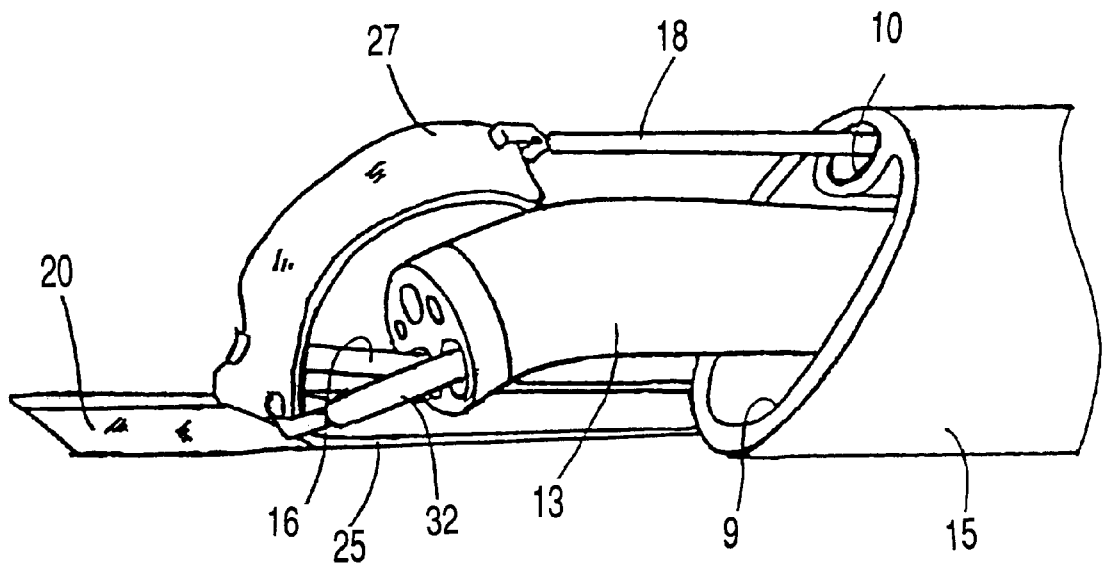
FIG. 10 is a schematic view illustrating a system according to a second embodiment of the invention.
Figure 11:
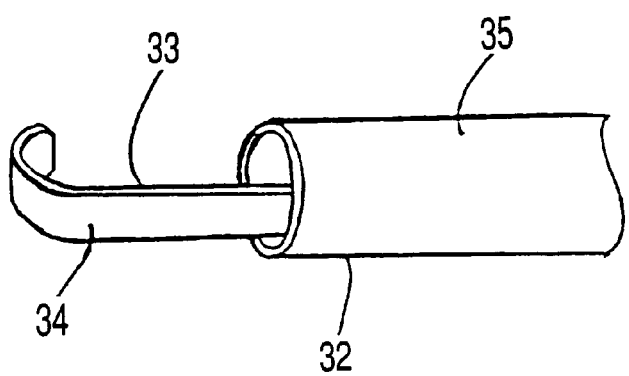
FIG. 11 is an enlarged view showing the distal end of a high frequency electric knife for use in the system of FIG. 10.

FIGS. 10 and 11 show an endoscopic treatment system according to a second preferred embodiment of the invention. This system has the same basic structure as the first embodiment.

FIG. 11 shows a high frequency electric knife 32 for use in the system of the second embodiment. The high frequency electric knife 32 has a high frequency cutting section 33, which is in the shape of a plate and has a J-shaped distal end. The high frequency cutting section 33 is arranged to protrude from and retreat into a sheath 21 in accordance with the movement of an operating section (not shown), which is connected to a high frequency power supply. The reverse surface of the high frequency cutting section 33 is coated with an insulating layer 34 made of a resin material that is represented by a fluorocarbon resin such as polytetrafluoroethylene. When cutting off a portion of esophagus mucous membrane using the system of this embodiment, a plurality of longitudinal incisions 25 and one circumferential incision 26 are formed in the esophagus mucous membrane, thereby forming a plurality of strip areas 27 in the mucous membrane of a to-be-removed portion, as in the first embodiment. After that, the forceps 16 and the high frequency electric knife 32 are inserted into the esophagus through the two channels of the endoscope 13 inserted in the endoscopic guide tube 15. Subsequently, while the strip area 27 is gripped with the forceps 16 and raised from the muscular tunics 20, it is incised by the high frequency electric knife 32 from the cardia 24 end (see FIGS. 5 and 6), i.e. in a reverse direction to that in the first embodiment. If an already separated portion of the strip area 27 interrupts the peeling operation, it is gripped with the forceps 18 inserted into the esophagus through the forceps guide channel 10, and shifted to a position in which it does not interrupt the peeling operation.

When cutting off certain mucous membrane in units of one strip area, how to handle an already separated portion of the mucous membrane significantly influences the working efficiency. In the system of this embodiment, the separated portion is gripped with the forceps inserted in the endoscopic guide tube, and therefore it does not interrupt the cutting operation. As a result, a high working efficiency can be achieved. Moreover, the portion of mucous membrane is peeled toward the throat, which facilitates finally cutting it off.

Figure 12:
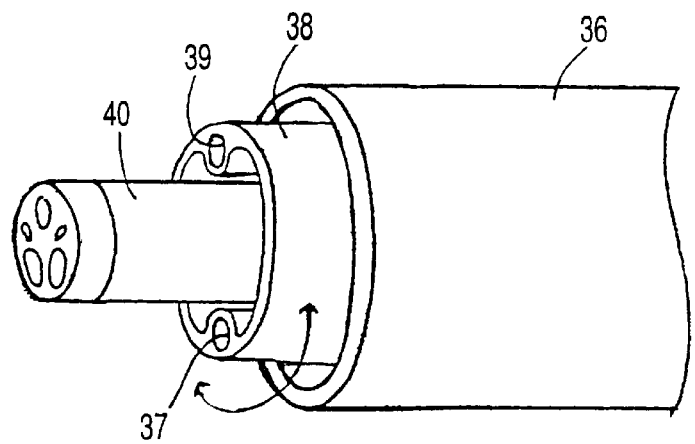
FIG. 12 is a view illustrating a modification of the system of FIG. 10, which includes an endoscopic guide tube of a double structure.

FIG. 12 shows a system according to a modification of the second embodiment. In this modification, an endoscopic guide tube 38 is located in an envelope 36. In other words, this system has substantially a double structure. The endoscopic guide tube 38 containing an endoscope 40 includes forceps guide channels 37 and 39 substantially diametrically opposed to each other. The endoscope 40 and the endoscopic guide tube 38 are rotatable and axially movable relative to each other. A gap defined therebetween is sealed with a sealing member (not shown). Furthermore, the endoscopic guide tube 38 is rotatable and axially movable relative to the envelope 36, and a gap defined therebetween is also sealed with a sealing member (not shown).

Arranging the endoscopic guide tube 38 movable in the envelope 36 improves the movability and hence operability of the endoscopic guide tube 38.

Figure 13:
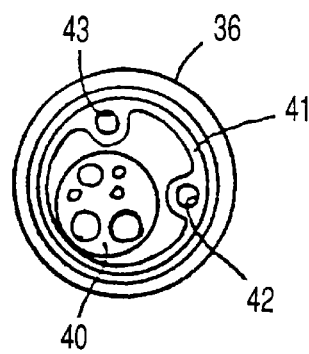
FIG. 13 is a view illustrating a modification of the endoscopic guide tube applicable to the system of FIG. 12.

FIG. 13 shows an endoscopic guide tube 41 according to another modification. The endoscopic guide tube 41 of this modification has two forceps guide channels 42 and 43 formed therein such that they are both located in one semicircle of a cross section of the tube 41 as shown in the figure (i.e. the channels 42 and 43 are not diametrically opposed to each other). Accordingly, the space for arranging the endoscope 40 therein can be enlarged. In other words, the endoscopic guide tube 41 can be made to have a smaller diameter than the endoscopic guide tube 38 which has the two forceps guide tubes 37 and 39 diametrically opposed to each other as shown in FIG. 12.

[Third Embodiment]

Figure 14:
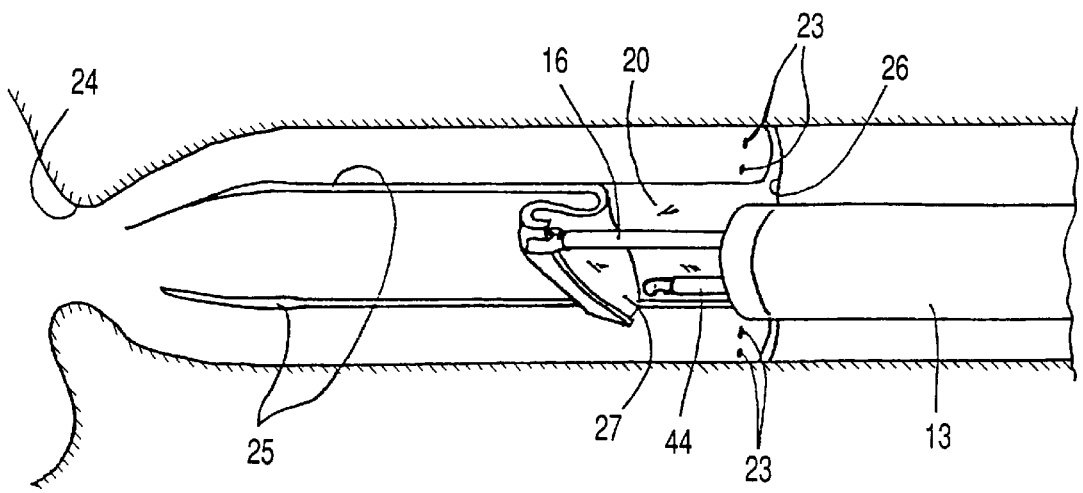
FIG. 14 is a view useful in explaining the step of separating a strip of mucous membrane of the esophagus, using a system according to a third embodiment.

FIG. 14 shows a system according to a third embodiment of the invention.

This system has substantially the same structure as the first embodiment except that the former does not employ any endoscopic guide tube. When cutting off a portion of esophagus mucous membrane, markings 23 and incisions 25 and 26 are formed in a predetermined portion of the esophagus mucous membrane, as in the first embodiment. Subsequently, the forceps 16 and a high frequency electric knife 44 are inserted into the esophagus through the two-channel endoscope 13. Then, the forceps 16 and the endoscope 13 are pushed into the stomach via the cardia 24, with a strip area 27 gripped with the forceps 16, thereby peeling off the strip area 27. If the strip area 27 cannot smoothly be peeled off muscular tunics 20, the peeling operation is executed while cutting the strip area 27 with the high frequency electric knife 44.

Since the system of this embodiment does not need any endoscopic guide tube, it has a simple structure and can execute operations easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic treatment system for executing peeling off or cutting off of a mucous membrane at a predetermined portion of an esophagus, comprising:

an endoscope having an insertion section provided with at least one channel therein, the endoscope being used for observing a target inner portion of a body;

a knife insertable into the channel of the endoscope for executing at least one of the peeling off and cutting off of the mucous membrane;

an endoscopic guide tube insertable into the esophagus, the endoscopic guide tube having a main channel in which the endoscope is insertable, and at least one sub channel entirely provided in the main channel; and a forceps that is insertable in the sub channel and that is used to grip the predetermined portion of the esophagus at which the mucous membrane is to be peeled off or cut off, wherein the mucous membrane is peeled off or cut off by the knife while the predetermined portion of the esophagus is gripped by the forceps.

2. The endoscopic treatment system according to claim 1, wherein the endoscopic guide tube includes:

a grip section arranged outside the body, an insertion section that is made of a soft transparent resin material, and that is insertable into the esophagus, and an opening formed in a side portion of the insertion section, which is close to the grip portion, and connecting the sub channel to outside, and wherein the endoscope includes an insertion section substantially longer than the insertion section of the endoscopic guide tube.

3. The endoscopic treatment system according to claim 1, wherein the flat knife has a curved cutting section coated with an insulating layer.

4. The endoscopic treatment system according to claim 1, wherein the insertion section of the endoscope has at least two channels formed therethrough.

5. The endoscopic treatment system according to claim 2, wherein the grip section of the endoscopic guide tube has a seal member that seals a gap between endoscopic guide tube and the endoscope inserted in the endoscopic guide tube.

6. The endoscopic treatment system according to claim 1, wherein the endoscopic guide tube has two sub channels.

7. The endoscopic treatment system according to claim 6, wherein the two sub channels are diametrically opposed to each other.

8. The endoscopic treatment system according to claim 6, wherein the two sub channels are both located in one semicircle of a cross section of the endoscopic guide tube.

9. The endoscopic treatment system according to claim 6, further comprising an envelope for inserting therein the endoscopic guide tube.

10. An endoscopic treatment system for executing at least one of localized injection into submucosa, peeling off of mucous membrane, and cutting off of mucous membrane at a predetermined portion of an esophagus, the system comprising:

an endoscope having an insertion section provided with at least one channel therein, the endoscope being used for observing a target inner portion of a body;

a plurality of treatment tools for treating the target inner portion, the treatment tools including a syringe needle for executing localized injection into submucosa, forceps for gripping a portion of mucous membrane, and at least one knife for executing at least one of peeling off and cutting off of mucous membrane, the at least one knife being one of a needle-shaped knife and a flat knife; and an endoscopic guide tube insertable into the esophagus, the endoscopic guide tube having a main channel into which the endoscope is insertable, and at least one sub channel into which each of the treatment tools is insertable;

wherein each of the treatment tools is approachable to the target inner portion via one of the endoscope and the endoscopic guide tube;

wherein the endoscopic guide tube has two sub channels; and wherein the endoscopic treatment system further comprises an envelope into which the endoscopic guide tube is insertable.

* * * * *

UNITED STATES PATENT AND TRADEMARK OFFICE
CERTIFICATE OF CORRECTION

PATENT NO.     : 6,527,753 B2
DATED          : March 4, 2003
INVENTOR(S)    : Ryuta Sekine et al.

It is certified that error appears in the above-identified patent and that said Letters Patent is hereby corrected as shown below:

<u>Title page,</u>
Item [73], Assignee, after "Olympus Optical Co., Ltd., Tokyo (JP),"
insert -- Mayo Foundation for Medical Education and Research, Rochester, MN (US) --.

Signed and Sealed this

Twenty-ninth Day of July, 2003

JAMES E. ROGAN
*Director of the United States Patent and Trademark Office*